United States Patent [19]

Fishel et al.

[11] 4,088,698

[45] May 9, 1978

[54] PRODUCTION OF THIOPHENOLS

[75] Inventors: Norman A. Fishel, Olivette; David E. Gross, St. Charles, both of Mo.

[73] Assignee: Monsanto Company, St. Louis, Mo.

[21] Appl. No.: 774,098

[22] Filed: Mar. 3, 1977

[51] Int. Cl.² .................................... C07C 148/02
[52] U.S. Cl. ........................................... 260/609 D
[58] Field of Search ..................... 260/609 D, 609 R

[56] References Cited

U.S. PATENT DOCUMENTS

| | | | |
|---|---|---|---|
| 2,116,182 | 5/1938 | Baur | 260/609 R |
| 2,438,838 | 3/1948 | Ballard et al. | 260/609 D |
| 3,042,724 | 7/1962 | Hoffenberg et al. | 260/609 D |

FOREIGN PATENT DOCUMENTS

| | | | |
|---|---|---|---|
| 913,585 | 12/1962 | United Kingdom | 260/609 D |

OTHER PUBLICATIONS

P. Sabatier, et al., Comptes Rendus, 150, (1910), pp. 1217-1221, 1569-1572.

*Primary Examiner*—Joseph Paul Brust
*Assistant Examiner*—Molly C. Eakin
*Attorney, Agent, or Firm*—Bruce Stevens

[57] ABSTRACT

A method for preparing thiophenolic compounds is described comprising reacting a phenol and hydrogen sulfide in the presence of a vanadia catalyst. It is preferred to carry out the process of this invention at low pressures, i.e. at pressures lower than 100 psi, atmospheric pressure being very suitable, although the process is operable at subatmospheric pressures. Preferred phenols, catalysts and reaction conditions are also described.

13 Claims, No Drawings

PRODUCTION OF THIOPHENOLS

BACKGROUND OF THE INVENTION

1. Field of the Invention

The present invention relates to a novel catalytic method for preparation of thiophenols from phenols and hydrogen sulfide at low, e.g. atmospheric pressure.

2. Prior Art

At least as far back as 1910 catalytic methods have been described for making thiols from alcohols and hydrogen sulfide, e.g. in Comptes Rendus, 150 (1910), pp. 1217-1221, Paul Sabatier and A. Mailhe, "General Method of Direct Preparation of Thiols By Catalysis, Starting From Alcohols." The catalyst was thoria and good thiol yields were obtained from primary alcohols, but the yields from secondary alcohols were about one third those of the primary alcohols. By passing a mixture of phenol or a cresol and hydrogen sulfide over thoria heated to between 430° and 480° C. the corresponding thiophenol was obtained; however, the yield obtained was less than that obtained with the alcohols and in the best case was only 17%. Above 500° C. the yield decreases due to destruction of $H_2S$.

In that same year 1910 another article was published by the same authors, Comptes Rendus, 150 (1910), pp. 1569-72, "On the Formation and Condensation of Thiols: Synthesis of Thioethers." A translation of a portion of this article reads as follows:

"In a recent communication we have shown a general method for the direct preparation of thiol, by the reaction of hydrogen sulfide and alcohol vapors in contact with thorium oxide above 300° C. This procedure, very advantageous for primary alcohols, gives poorer yields with secondary alcohols, and its results are less satisfying for phenols for which a very high temperature is required and only very mediocre yields are obtained."

"There was a certain interest to learn if the other anhydrous metallic oxides which our previous research had shown as capable of causing catalysis of alcohols, would be more or less preferable to thoria for the direct synthesis of thiols. From this point of view, we have examined two oxides which are exclusively dehydration catalysts, alumina and the blue oxide of tungsten, and various oxides which are mixed dehydration and dehydrogenation catalysts, chromium oxide, zirconium oxide, uranium oxide and the blue oxide of molybdenum, all used in their most active form."

"For phenol itself, the temperature of the oxide being in the vicinity of 450° C., the thiophenol yield was lower in every case. The yields found were:

Aluminum oxide — 0.4%
Zirconium oxide — 1.5%
Blue molybdenum oxide — 1.8%
Blue tungsten oxide — 1.5%
Chromium oxide — 2.5%
Uranium oxide — 3.8%

Thoria gave a yield of 8% and therefore was confirmed as being very superior to the other oxides, the same as for alcohols."

In U.S. Pat. No. 2,116,182, Baur, patented May 3, 1938, "Production of Mercaptans", production of aliphatic mercaptans of high molecular weight is described and carried out by reacting an alcohol and hydrogen sulfide in the presence of a dehydration catalyst. The catalysts which are shown in the experimental examples are zirconium dioxide which it is stated may be supported on pumice, activated charcoal which can be impregnated with phosphoric acid to improve activity, aluminum oxide and granulated titanium dioxide. In the patent, column 1, lines 36 to column 2, line 5, the catalysts are discussed more broadly as to what other catalysts may be useful.

In U.S. Pat. No. 2,438,838, Ballard et al., patented Mar. 30, 1948, "Process for the Production of Thiophenols" a process is described involving reacting a phenol with hydrogen sulfide at superatmospheric pressure in the presence of a metal oxide dehydration catalyst.

Superatmospheric pressure is described in column 1, line 41 to column 2, line 10, which are generally described as above 200 psi as being sufficient, and in most cases pressures above about 300 psi are preferred. The patent goes on to say that pressures above approximately 400 psi have been found effective in producing substantial yields at temperatures between 400° C. and about 600° C. Catalysts which may be used are broadly discussed beginning in column 2, line 46 and continuing through column 4, line 22. In the experimental examples only two catalysts were used; namely, activated bauxite and activated alumina.

None of the above prior art experimentally tried the particular catalyst, vanadium oxide, which is the catalyst used in the process of this invention, and in only one of the reference is vanadium oxide mentioned in the broad teachings, namely U.S. Pat. No. 2,116,182, column 1, line 43 involving a process for the production of mercaptans, not thiophenols. Clearly the process of this invention is both novel and unobvious over the teachings of the prior art.

SUMMARY OF INVENTION

A method for preparing thiophenolic compounds is described comprising reacting a phenol and hydrogen sulfide in the presence of a vanadia catalyst. It is preferred to carry out the process of this invention at low pressures, i.e. at pressures lower than 100 psi, atmospheric pressure being very suitable, although the process is operable at subatmospheric pressures. Preferred phenols, catalysts and reaction conditions are also described.

It is an important object of the present invention to provide a selective process for the production of thiophenols in high yield.

Another object of this invention is to provide a process for the production of thiophenols which can be conducted in a batch or continuous manner.

Another object of this invention is a process for the production of thiophenols at low, particlarly atmospheric, pressure.

These and other objects and advantages of the present invention will become apparent in view of the following detailed description which covers a number of preferred embodiments thereof.

DESCRIPTION OF THE PREFERRED EMBODIMENTS

The objects of the present invention are accomplished by a process of forming thiophenols at elevated temperatures with a vanadium oxide catalyst. Under the influence of the catalyst one molecule of a phenol reactant and one hydrogen sulfide molecule combine to form a thiophenol and water. It will, therefore, be understood that phenol, derivatives of phenol, and other phenolic compounds can be used in the process of the present invention. The ratio (molar) of hydrogen sulfide to phenolic compound in the reaction mixture to the reactor should be in the range of 0.1:1 to 20:1 or more, preferably 0.7:1 to 10:1.

It should be understood that the phenolic reactants used for the process of this invention may be either unsubstituted, that is phenol, or substituted in one or more positions on either side of the hydroxyl group that is in the 2, 3, 4, 5 or 6 positions, or on any side chain associated with the aromatic nucleus. Thus as it will be readily appreciated, the phenolic reactants may be substituted in many different ways with a wide variety of substituents, subject to the usual reservation that the said substituents are non-interfering substituents. That is to say, the phenolic reactants should not have substituents which would substantially interfere with the present process for the direct preparaton of thiophenols from phenols and hydrogen sulfide, for instance, by poisoning the catalyst; however, the catalysts of the invention are especially resistant to poisoning.

Thus, unless otherwise indicated herein, phenols and like expressions such as phenolic compounds or reactants are employed in the generic sense and are intended to include phenol or phenol substituted in the manner previously described. Thus the generic term phenols may be taken to include phenol itself, alkyl substituted phenols, hydroxy substituted phenols, aryl substituted phenols, polycyclic phenols and the like. Suitable alkyl substituted phenols include all alkyl groups, however, it is preferred to use alkyl substituted phenols wherein the alkyl group contains between one and six carbon atoms, more preferably between one and three carbon atoms such as ortho, meta, and paracresol; ortho, meta, and para ethylphenol; 2,5-xylenol, 2,3-xylenol, 2,4-xylenol and 3,4-xylenol. When the alkyl group contains more than two carbon atoms, it may be straight or branched chain as, for example, the alkyl group may be either n-propyl or isopropyl. In a similar manner, suitable hydroxy substituted phenols include all phenolic compounds including phenols substituted with several hydroxy groups such as pyrocatechol, resorcinol, hydroquinone or pyrogallol. Finally suitable polycyclic phenols include such materials as 1-naphthol and 2-naphthol.

Inasmuch as the instant process is preferably carried out in the vapor phase, the phenolic starting material should preferably be a vaporizable material. That is, the reactant should have sufficient thermal stability for vaporization without decomposition at atmospheric pressure and its boiling point. The aforesaid phenols typically have such characteristics.

A catalyst is essential in the practice of this invention, and as such, must be a material capable of catalyzing the reaction of the phenolic compounds with hydrogen sulfide to form thiophenols in high yield. Vanadium oxide ($V_2O_5$), has been found very active as a catalytic material and can be used as is, or in combination with other materials such as supports which are sufficiently refractory to withstand the elevated reaction temperature at which the reaction is preferably conducted. The extent of desired reactions obtained by using less than 1% by weight of the vanadium oxide on a support is perceptible but not sufficient to be of any appreciable value. Vanadium oxide which is essentially pure may be used as the active catalytic material. If desired the catalyst may be charged to the reactor as an oxide or converted or regenerated to the oxide in situ prior to use in the process of the invention. In accordance with various practices of the art, the active catalyst may be used unsupported, or dispersed or supported on a suitable carrier material, such as alumina, silicaalumina (e.g. 50-95% silica), silica, or the like.

A supported catalyst can typically be prepared, using the following method. Prepare a solution comprised of an appropriate amount of a soluble vanadium compound dissolved in distilled water, or other suitable solvent, and diluted to the desired volume, preferably in excess of the solution absorptivity of the support. The support is intermingled with said solution and the resulting mixture is stirred for about ten minutes at ambient conditions. Excess solvent is slowly removed by stirring and passing a soft air flow over the preparation to give a free-flowing material. Mild heating may also be employed to assist in excess solvent removal. The preparation is finally dried over a period of about 18 hours at about 120° C. in a forced air oven followed by air calcination conducted at a temperature in the range of about 450° to 600° C. for about 5 hours.

A typical method for preparing nominally 100% vanadium oxide catalyst follows. Vanadia powder is obtained by air calcination of a suitable precursor powder, e.g., ammonium metavanadate or vanadyl hydroxide. The calcination is conducted at an appropriate temperature depending on the precursor selected, that is at a temperature in the range of about 300° to 500° C for a period of about 5 hours. The freely flowing vanadia powder is screened, tumble-mixed with about 2% by weight graphite and the composite material is pressed into pellets. The formed catalyst is air calcined at a temperature in the range of about 450° to 600° C for about 5 hours, especially to remove the graphite component. This and other methods known to those skilled in the art of physically forming catalysts can be used.

For the reaction of the invention, the phenolic reactants and hydrogen sulfide are introduced into the reaction vessel containing the catalyst which is maintained at a temperature high enough to vaporize the phenolic reactant, or alternatively the phenolic reactant can be vaporized prior to introduction to reaction vessel, and also high enough to induce a good reaction rate so that an adequate yield of the product may be obtained at reasonable space velocities as hereinafter described. On the other hand, it is preferred that the temperature should not be raised so high that the yield drops off or decomposition of the products or starting materials occurs. In general the reaction temperature is desirably above about 300° C. or about 300° to 700° C. The preferred temperature range, however, will depend somewhat on the starting materials and the products in relationship to their susceptibility to decomposition and like factors as discussed above. In particular for phenol the reaction temperature is preferably above about 350° C. with optimum results being obtained within the range of about 400° to 600° C. The temperature of the reaction chamber may be controlled in conventional manner such as by an electrically heated jacket, to maintain the desired operating temperature, or by other convention means.

Reaction pressure is preferably low, below about 100 psi, and more preferably at about atmospheric pressure, although subatmospheric pressure can be used. In general, atmospheric pressure is preferred for convenience, simplicity, and economy in carrying out the reaction.

The process of this invention may be effected in any suitable manner and, for example, may comprise either a batch or continuous type operation. When a batch type operation is used, a quantity of the starting materials suitable for the capacity of the reaction vessel (reactor) employed are placed in an appropriate apparatus along with the catalyst. The particular reaction vessel may comprise a glass or metal flask or its commerical counterpart. Following this the reactor and contents thereof are heated to the desired operating temperature which is above 300° C. and maintained thereat for a predetermined period of time which may range from about 0.5 hours up to 10 hours or more in duration. While the period of time necessary to conduct the reaction depends upon parameters such as the activity of the catalyst, the reaction temperature, the reaction pressure, and the like, it must be an effective period of time, which may of course be limited in duration if the starting materials or products tend to decompose under the reaction conditions. At the end of the reaction period, the reactor contents are allowed to return to room temperature, the excess pressure discharged, if any, and the reaction mixture recovered. If the reaction vessel is a flask, the reaction mixture is treated in a similar manner, that is, by allowing the flask contents to return to room temperature after the reaction period, followed by recovery of the reaction mixture. The reaction product may be separated from the catalyst by conventional means such as filtration.

It is also contemplated within the scope of this invention that the process described herein may be effected in a continuous manner. One particular method comprises a fixed bed operation in which the reactant feed stream is continuously charged to a reactor containing a fixed bed of catalyst, the reactor being maintained, at the desired operating temperature, broadly 300° to 700° C., preferably about 400° to 600° C., thereby allowing the heated reactants to contact the heated catalyst. Other means of accomplishing a continuous operation are by using the catalyst in a moving bed system or a fluidized bed system; however, in view of the well known operational advantages, it is preferred to use a fixed bed system. The reactor may be operated at subatmospheric, atmospheric, or above atmospheric pressure, e.g., from about 2 to 100 psi. The reactants may be passed over the catalyst bed in either upward or downward flow for example, and the products withdrawn continuously, allowed to cool, and recovered. In the event it is desired to operate the reactor at subatmospheric or above atmospheric pressure conventional means for obtaining such condition, for example, by use of mechanical vacuum pumps or mechanical compressors may be employed.

The space velocity of the reactants through the active catalyst zone may vary considerably depending upon for example, the reactivity of the starting material, the activity of the catalyst, and the reaction temperature. In addition, the reaction mixture may be recycled separately over a single catalyst mass or sequentially passed over several catalysts of the same or different composition. However, high yields per pass are obtainable and it is usually preferred to recycle only the unreacted phenol and hydrogen sulfide in the product stream after the product has been separated therefrom. The gas hourly space velocity (GHSV) is preferably selected from the range of about 1 $hr^{-1}$ to 3000 $hr^{-1}$, more preferably 20 $hr^{-1}$ to 800 $hr^{-1}$ space velocities. GHSV is defined as the gas volume of reactants (standard conditions of temperature and pressure) per volume of catalyst per hour.

After a period of operation when the catalyst may become deactivated by the presence of carbonaceous deposits, the catalyst may be reactivated or regenerated by passing an oxygen containing gas, for example air, air mixed with nitrogen, or air mixed with steam, into contact with the catalyst at an elevated temperature in order to burn carbonaceous deposits from the catalyst e.g. temperatures of 300° to 1000° C. may be employed. The method of regenerating the catalyst will depend on whether there is a fixed bed, moving bed, or fluidized bed operation. Regeneration methods and conditions are well known in the art. Catalyst may also be pretreated with gas containing hydrogen sulfide or carbonyl sulfide. All of the experiments reported hereinbelow were carried out in fixed bed catalyst reactors.

The following examples are given to illustrate the process of the present invention, and are not intended to limit the generally broad scope of the present invention.

EXAMPLE 1

Phenol is vaporized and fed to the reactor at a rate equivalent to 80 $hr^{-1}$ gas hourly space velocity. The phenol was mixed with $H_2S$ being fed at a rate equivalent to 80 $hr^{-1}$ gas hourly space velocity and the mixture passed over a catalyst bed maintained at 550° C. The catalyst as charged to the reactor contained 8% by weight $V_2O_5$ dispersed on a diatomite silica support. The reactor effluent was cooled, the liquid product separated from the vapor (mostly unreacted $H_2S$), and the liquid product was analyzed by gas chromatography. The phenol conversion was 48% and the selectivity to thiophenol was 75%. The thiophenol product and unreacted phenol can each be separated from the liquid product by distillation, and the unreacted, recovered phenol can be recycled to the reactor together with unreacted hydrogen sulfide. Most of the unreacted hydrogen sulfide is not condensed and can readily be recycled in gaseous phase to the reaction.

EXAMPLE 2

The conditions of Example 1 are repeated except the catalyst bed is maintained at 400° C. and the catalyst contained 10% by weight $V_2O_5$ dispersed on a silica-aluminasupport. The phenol conversion was 35% and the selectivity to thiophenol was 80% from analysis of the liquid product recovered.

EXAMPLE 3

The conditions of Example 1 are repeated except the catalyst bed is maintained at 500° C. and the catalyst is a medium surface area alumina (80 $m^2/g$). Analysis of the product showed it to contain a number of components but less than 2% thiophenol and phenyl sulfide.

EXAMPLE 4

Phenol was charged to the reactor at a rate equivalent to 50 GHSV and $H_2S$ at a rate equivalent to 40 GHSV. The catalyst was silica maintained at 500° C. Total phenol conversion was about 2% with essentially no thiophenol.

EXAMPLE 5

A catalyst containing 10% by weight $V_2O_5$ dispersed on a silica-alumina support was maintained at 350° C. Resorcinol was fed at a rate equivalent to a rate of 30 GHSV and $H_2S$ fed at a rate of 105 GHSV. Analysis of the liquid product showed 24% resorcinol conversion and a 50% selectivity to m-hydroxybenzenethiol. The m-hydroxybenzenethiol product, unreacted resorcinol and unreacted hydrogen sulfide can each be separated from the liquid product by distillation, and the unreacted, recovered resorcinol and hydrogen sulfide can be recycled to the reactor. The other hydroxy group of the m-hydroxybenzenethiol can be converted to a thiol group, if desired, by recycle of the m-hydroxybenzenethiol product or higher temperatures, higher $H_2S$/resorcinol ratios and/or lower GHSV.

Thiophenols are well known in the art and have many uses such as anthelminthics, polymerization stabilizers, complexing agents for metal extraction or flotation benefaction, flame resistant polymers; rubber chemicals, such as accelerators, inhibitors, anti-oxidants and anti-ozonants; fragrances and flavors, arctic oils and as intermediates for making other compounds such as the insecticide described in U.S. Pat. Nos. 2,988,474 and 3,642,960 patents. Although the invention has been described in terms of specified embodiments which are set forth in considerable detail, it should be understood that this is by way of illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed is:

1. A process for the production of thiophenols comprising reacting a phenol and hydrogen sulfide in vapor phase at a temperature in the range of 300° C. to 700° C. at a gas hourly space velocity of from 1 $hr^{-1}$ to 3,000 $hr^{-1}$ over a vanadium oxide catalyst to give a crude vapor product containing a thiophenol.

2. A process of claim 1 carried out at a pressure of less than 100 psi.

3. A process of claim 2 wherein the pressure is about atmospheric pressure.

4. A process of claim 1 wherein said phenol is phenol and which thiophenol is thiophenol.

5. A process of claim 1 wherein the catalyst comprises vanadium oxide dispersed on a support.

6. A process of claim 1 wherein the catalyst comprises vanadium oxide dispersed on a support selected from the group consisting of silica, silica-alumina and alumina.

7. A process of claim 1 wherein said phenol is resorcinol and said thiophenol is m-hydroxybenzenethiol.

8. A process of claim 1 wherein the molar ratio of hydrogen sulfide to phenol in the reaction mixture is preferably in the range of 0.7:1 to 10:1.

9. A process of claim 1 wherein the reaction temperature is preferably in the range of 400° C to 600° C.

10. A process of claim 1 wherein the gas hourly space velocity is preferably in the range of 20 $hr^{-1}$ to 800 $hr^{-1}$.

11. A process of claim 1 wherein the crude vapor product is cooled and a crude liquid product is separated from a vapor comprising unreacted hydrogen sulfide.

12. A process of claim 11 wherein a thiophenol product is separated from the crude liquid product by distillaton.

13. A process of claim 11 wherein unreacted phenol reactant is separated from the crude liquid product by distillation and the unreacted, separated phenol is recycled to the reactor together with unreacted hydrogen sulfide.

* * * * *